(12) United States Patent
Caduff et al.

(10) Patent No.: US 7,534,208 B2
(45) Date of Patent: May 19, 2009

(54) DEVICE FOR THE MEASUREMENT OF GLUCOSE CONCENTRATIONS

(75) Inventors: Andreas Caduff, Zurich (CH); Yuri Feldman, Jerusalem (IL)

(73) Assignee: Max Link, Zurich (CH)

( * ) Notice: Subject to any disclaimer, the term of this patent is extended or adjusted under 35 U.S.C. 154(b) by 167 days.

(21) Appl. No.: 11/070,859

(22) Filed: Mar. 2, 2005

(65) Prior Publication Data
US 2005/0203363 A1  Sep. 15, 2005

Related U.S. Application Data

(63) Continuation of application No. PCT/IB02/03935, filed on Sep. 24, 2002.

(51) Int. Cl.
*A61B 5/00* (2006.01)
*G01V 3/00* (2006.01)
(52) U.S. Cl. .................. 600/365; 600/309; 324/301; 324/306; 324/321; 324/322
(58) Field of Classification Search ............... 600/365, 600/309, 300, 301, 366; 324/301, 307, 308, 324/312, 318, 321, 322; 335/302
See application file for complete search history.

(56) References Cited

U.S. PATENT DOCUMENTS

| | | | |
|---|---|---|---|
| 4,509,531 A | | 4/1985 | Ward |
| 4,679,426 A | | 7/1987 | Fuller et al. |
| 4,765,179 A | | 8/1988 | Fuller et al. |
| 4,875,486 A | * | 10/1989 | Rapoport et al. ............ 600/415 |
| 5,050,612 A | | 9/1991 | Matsumura |
| 5,072,732 A | * | 12/1991 | Rapoport et al. ............ 600/415 |
| 5,077,476 A | | 12/1991 | Rosenthal |
| 5,109,855 A | | 5/1992 | Gunter |
| 5,353,802 A | | 10/1994 | Ollmar |
| 5,508,203 A | | 4/1996 | Fuller et al. |
| 5,771,891 A | | 6/1998 | Gozani |

(Continued)

FOREIGN PATENT DOCUMENTS

AT  395 075  9/1992

(Continued)

OTHER PUBLICATIONS

English Abstract of AT 395 075 dated Sep. 10, 1992.

(Continued)

*Primary Examiner*—Charles A Marmor, II
*Assistant Examiner*—Navin Natnithithadha
(74) *Attorney, Agent, or Firm*—Ladas & Parry LLP

(57) ABSTRACT

The device of the present invention comprises a ring (1) of a ferrite material and two coils (4, 5) wound around it. A alternating current is fed to one of the coils (4). This current gives rise to an alternating magnetic field within and along the ring, which in turn generates an alternating electric field. A specimen (3) is placed in the alternating electric field. The dielectric properties of the specimen (3) affect the electric field, which in turn induces a magnetic field and generates currents in the coils (4, 5). As the dielectric properties of the specimen (3) depend on its glucose level, the glucose level can therefore be measured by determining a parameter depending on the inductances of the coils.

19 Claims, 2 Drawing Sheets

U.S. PATENT DOCUMENTS

| | | | |
|---|---|---|---|
| 5,792,668 A | 8/1998 | Fuller et al. | |
| 5,804,967 A | 9/1998 | Miller et al. | |
| 5,890,489 A | 4/1999 | Elden | |
| 5,978,694 A * | 11/1999 | Rapoport | 600/407 |
| 6,028,433 A | 2/2000 | Cheiky-Zelina et al. | |
| 6,182,504 B1 | 2/2001 | Gaisford | |
| 6,309,884 B1 | 10/2001 | Cooper et al. | |
| 6,356,776 B1 | 3/2002 | Berner et al. | |
| 6,517,482 B1 | 2/2003 | Elden et al. | |
| 6,565,509 B1 | 5/2003 | Say et al. | |
| 6,723,048 B2 * | 4/2004 | Fuller | 600/365 |
| 6,794,865 B2 * | 9/2004 | Astley et al. | 324/306 |
| 7,239,904 B2 * | 7/2007 | Hirao | 600/316 |
| 2002/0106709 A1 | 8/2002 | Potts et al. | |
| 2002/0155615 A1 | 10/2002 | Novikov et al. | |
| 2003/0153821 A1 | 8/2003 | Berner et al. | |
| 2004/0104736 A1 | 6/2004 | Cohen et al. | |
| 2004/0133353 A1 | 7/2004 | Geutebruck | |
| 2004/0147819 A1 | 7/2004 | Caduff et al. | |
| 2004/0240512 A1 | 12/2004 | Pesach | |
| 2005/0101842 A1 | 5/2005 | Suda | |
| 2005/0113662 A1 | 5/2005 | Kjennati et al. | |
| 2005/0171415 A1 * | 8/2005 | Hirao | 600/316 |

FOREIGN PATENT DOCUMENTS

| | | |
|---|---|---|
| DE | 30 17 168 | 11/1981 |
| DE | 100 35 415 | 1/2002 |
| EP | 0 298 441 | 1/1989 |
| EP | 0 309 085 | 3/1989 |
| EP | 0 266 434 | 10/1995 |
| EP | 1 092 386 | 4/2001 |
| GB | 2 033 575 | 5/1980 |
| GB | 2 055 206 | 2/1981 |
| GB | 1 599 241 | 9/1981 |
| GB | 2 100 864 | 1/1983 |
| JP | 62-83649 | 4/1987 |
| JP | 9-201337 | 8/1997 |
| JP | 2000-162176 | 6/2000 |
| RU | 2 069 863 | 11/1996 |
| RU | 2 073 242 | 2/1997 |
| RU | 2 088 927 | 8/1997 |
| SU | 1698724 | 12/1991 |
| WO | 85/04481 | 10/1985 |
| WO | 93/18395 | 9/1993 |
| WO | 93/18402 | 9/1993 |
| WO | 95/04496 | 2/1995 |
| WO | 97/39341 | 10/1997 |
| WO | 98/04190 | 2/1998 |
| WO | 98/09566 | 3/1998 |
| WO | 99/39627 | 8/1999 |
| WO | 99/44495 | 9/1999 |
| WO | 00/09996 | 2/2000 |
| WO | 00/43759 | 7/2000 |
| WO | 01/36952 | 5/2001 |
| WO | 01/47415 | 7/2001 |
| WO | 02/062214 | 8/2002 |
| WO | 02/069791 | 9/2002 |
| WO | 02/073179 | 9/2002 |
| WO | 03/017834 | 3/2003 |

OTHER PUBLICATIONS

English Abstract of DE 100 35 415 dated Jan. 31, 2002.
English Abstract of EP 1 092 386 dated Apr. 18, 2001.
Patent Abstracts of Japan of JP 9-201337 dated Aug. 5, 1997.
Patent Abstracts of Japan of JP 2000-162176 dated Jun. 16, 2000.
Patent Abstracts of Japan of JP 62-83649 dated Apr. 17, 1987.
Derwent Abstract of RU 2 069 863 dated Nov. 27, 1996.
English Abstract of RU 2 073 242 dated Feb. 10, 1997.
English Abstract of RU 2 088 927 dated Aug. 27, 1997.
Derwent Abstract of SU 1698724 dated Dec. 15, 1991.
Khalil, O. S. "Non-Invasive Glucose Measurement Technologies: An Update from 1999 to the Dawn of the New Millennium" *Diabetes Technology & Therapeutics* (2002) vol. 6, No. 5, pp. 660-695.
Choleau, C. et al. "Prevention of Hypoglycemia Using Risk Assessment With a Continuous Glucose Monitoring System" *Diabetes* (2002) vol. 51, pp. 3263-3273.
Feldman, Y. "Time Domain Dielectric Spectroscopy: An Advanced Measuring System" *Rev. Sci. Instrum.* (1996) vol. 67, No. 9, pp. 3208-3216.
Feldman, Y. D. et al. "Time Domain Dielectric Spectroscopy. A New Effective Tool for Physical Chemistry Investigation" *Colloid & Polymer Science* (1992) vol. 270, No. 8, pp. 768-780.
General Linear Least Squares in "Numerical Recipes in C: The Art of Scientific Computing" *Cambridge University Press. Programs* (1988) Chapter 15, pp. 671-681.

* cited by examiner

DEVICE FOR THE MEASUREMENT OF GLUCOSE CONCENTRATIONS

This is a continuation of International Application No. PCT/IB2002/03935 filed Sep. 24, 2002 which designated the U.S., claims the benefit thereof and incorporates the same by reference.

TECHNICAL FIELD

The invention relates to a device and a method for the measurement of a glucose level according to the preamble of the independent claims.

BACKGROUND ART

It has been known to measure glucose concentrations in living tissue using electric fields. In particular, it has been found that the dielectric properties of the tissue vary with glucose concentration. Corresponding devices rely on the application of electrodes to the human body, which gives rise to various boundary problems, such as a dependence of the results on current skin condition.

DISCLOSURE OF THE INVENTION

Hence, it is a general object of the invention to provide a device and a method described above that is less prone to boundary problems.

This object is achieved by the device and method according to the independent claims.

Hence, the device of the present invention comprises a ring and a coil assembly. A coil of the coil assembly is wound around the ring, i.e. the ring is forming a substantially toroidal core of the coil. The coil may form part or all of the coil assembly. A current source is provided for generating an AC current in the coil. This current gives rise to an alternating magnetic field within and along the ring, which in turn generates an alternating electric field. A specimen is placed in the alternating electric field. In this way it is possible to generate an electric field within the specimen without using electrodes.

The dielectric properties of the specimen affect in turn the alternating electric field, which in turn affects the magnetic field and the inductance of the coil assembly. Hence, any parameter that depends on the inductance of the coil assembly also depends on the dielectric properties of the specimen and therefore on the glucose level. Therefore, by measuring a signal depending on the inductance of the coil assembly and by using suited calibration data, the glucose level can be determined.

The coil assembly may consist of a single coil, in which case the mentioned inductance is the coil's self inductance. Preferably, however, the coil assembly comprises two or more coils, and the mentioned inductance is a mutual inductance of the two coils, which can e.g. be measured by applying a voltage to a first one of the coils and measuring the induced voltage or current in the second coil.

BRIEF DESCRIPTION OF THE DRAWINGS

The invention will be better understood and objects other than those set forth above will become apparent when consideration is given to the following detailed description thereof. Such description makes reference to the annexed drawings, wherein.

MODES FOR CARRYING OUT THE INVENTION

Figure 1:
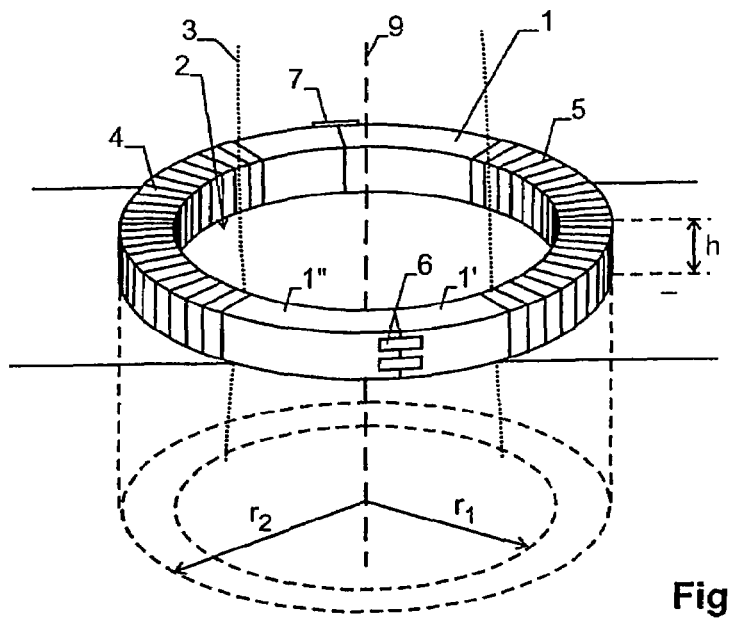
FIG. 1 shows an embodiment of a toroid coil assembly according to a first embodiment of the invention.
Figure 2:
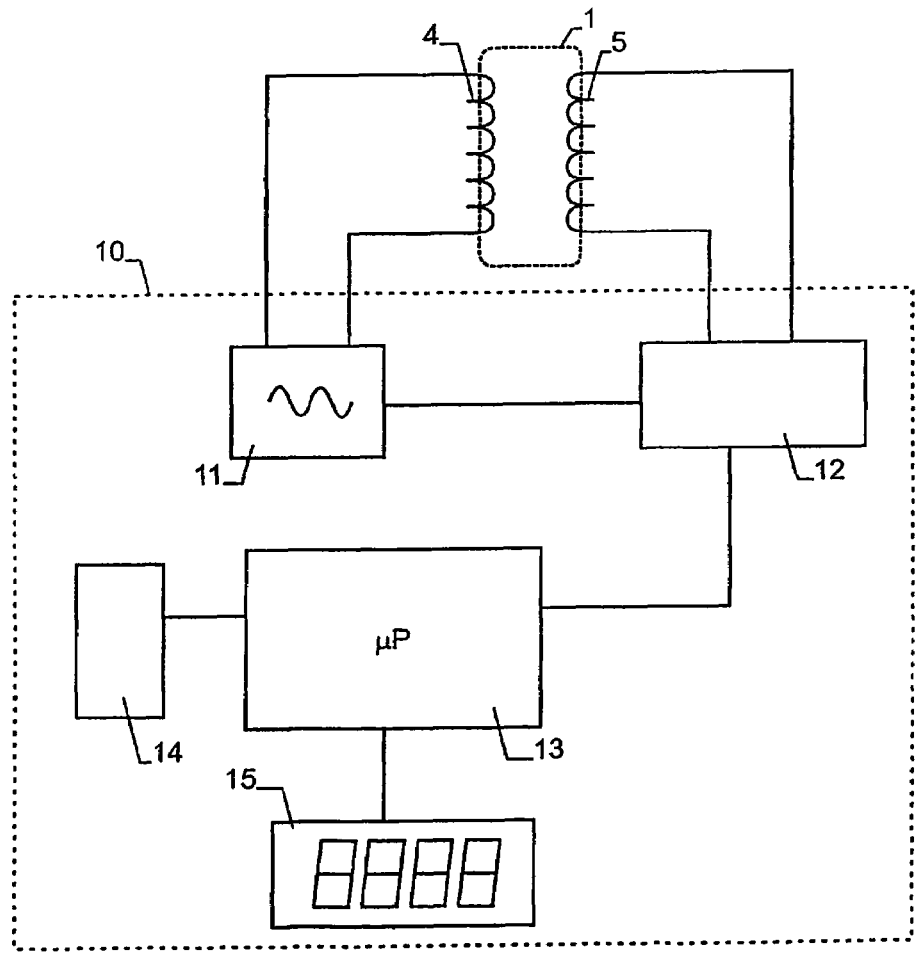
FIG. 2 shows a block diagram of a circuit for operating the coil assembly of FIG. 2.

A coil assembly for a device according to a first embodiment of to the invention is shown in FIGS. 1 and 2. The device comprises a ring 1 with a central opening 2 for receiving a specimen 3 to be measured, such as a patient's finger or arm. Two coils 4, 5 of a coil assembly are wound. i.e., looped through the central opening, onto ring 1, each coil forming part of a toroid or a complete toroid.

For being placed on specimen 3, ring 1 can consist of two parts 1', 1" that can be separated at least at one point. FIG. 1 shows the two parts to be connected at one end by flexible hinges 6 and at an opposite end by a releasable lock 7.

Ring 1 should be made of a material of high magnetic permeability $\mu$, such as a ferrite. Materials with a permeability of at least 100, preferably of at least 1000, should be used.

An electronic circuit 10 such as shown in FIG. 2 may be used for operating the coil assembly of FIG. 1. Electronic circuit 10 may e.g. be arranged in a common housing (not shown) with ring 1.

The circuit comprises an AC voltage generator 11, which is preferred to be a sine wave generator operating at a given frequency f, preferably of at least 1 kHz. AC voltage generator 11 feeds a current through first coil 4, which generates an alternating magnetic field in ring 1. As mentioned above, this magnetic field gives in turn rise to an alternating electric field in opening 2 interacting with the dielectric properties of specimen 3. In particular; dipoles are oriented and ions are separated creating addition induced polarization, which affects the magnetic field in ring 1 and therefore induces additional current components in the coils 4 and 5.

In other words, the dielectric properties of specimen 3 affect the self inductances $L_{ii}$ as well as the mutual inductances $L_{ij}$ of the coils 4 and 5.

The voltage over second coil 5 is fed to a detector 12. Detector 12 can e.g. measure the ratio $\tilde{K}$ between the voltage $\tilde{V}_2$ and $\tilde{V}_1$. As can be shown, this ratio is given by $$\tilde{K}(\omega) = \frac{\tilde{V}_2(\omega)}{\tilde{V}_1(\omega)} = \frac{W_2}{W_1} \cdot \frac{1}{1 + \tilde{Q}(\omega)} \text{ with} \tag{1}$$

$$\tilde{Q}(\omega) = \pi \cdot \omega^2 \varepsilon_0 \mu_0 \varepsilon_c^*(\omega) \mu^*(\omega) \cdot h \cdot d \cdot \frac{r_1}{r_2} \cdot \frac{\langle r \rangle}{r_2 - r_1} \frac{1}{W_2} \tag{2}$$

wherein $W_1$ is the number of turns in coil 4;

$W_2$ is the number of turns in coil 5;

$\varepsilon_0$ is the dielectric permittivity of free space ($8.85 \cdot 10^{12}$ F/m)

$\mu_0$ is the magnetic permeability of free space ($4\pi \cdot 10^{-7}$ H/m)
$\epsilon_c^*(\omega)$ is the relative complex dielectric permittivity of the specimen including the DC-conductivity term, i.e.

$$\varepsilon_c^*(\omega) = \varepsilon^*(\omega) - \frac{\sigma}{i\varepsilon_0 \omega} \qquad (3)$$

$\sigma$ is the DC-conductance of the specimen [$1/\Omega$m],
$\mu^*(\omega)$ is the relative complex magnetic permeability of ring 1;
the geometrical parameters of the ferrite core $r_1$, $r_2$, and h are shown in FIG. 1, and $$d = r_2 - r_1, \text{ and } \langle r \rangle = \frac{r_1 + r_2}{2}.$$

Equation 2 is based on the assumption that the specimen is cylindrical with a diameter of $2 \cdot r_1$ and a height of h and is centered in opening 2 of ring 1. For a differently shaped specimen (as will be the rule for invivo measurements) a suited correction factor has to be applied. Such a correction factor is automatically accounted for when using the calibration technique described below.

The ratio $\widetilde{K}$ as measured by detector 12 is converted to a digital signal and fed to a microprocessor 13, which converts it to a glucose concentration using calibration data stored in a non-volatile memory 14. The glucose concentration can e.g. be displayed on a display 15.

For calibrating the present device, several measurements at known glucose levels $c_{gl}$ are carried out for a given patient. For each measurement, the known glucose level is stored together with the voltage ratio $\widetilde{K}$. After a number of measurements, the relation between ration $\widetilde{K}$ and glucose level can be fitted to a function f using one or more parameters p1, p2, ..., i.e. $c_{gl} = f(\widetilde{K}, p1, p2 ...)$. The parameters p1, p2 ... can be stored as calibration data in memory 14. The function $f(\widetilde{K})$ can e.g. be a straight line (i.e. $f(\widetilde{K}, p1, p2) = p1 + \widetilde{K} \cdot p2$) or any other function that is found empirically or theoretically to be suitable to describe the relation between $\widetilde{K}$ and $c_{gl}$.

Instead of measuring the voltage ratio $\widetilde{K}$, any other parameter depending on the mutual inductance $L_{ij}$ of the coils 4 and 5 can be measured. Similarly, any parameter depending on the self inductance of one of the coils can be measured, in which case only a single coil is required. For example, coil 4 may be part of an LC-circuit of an oscillator operating at approximately 50 MHz. A change in the coil's self inductance will lead to a change of the oscillator's frequency, which can be measured easily.

Figure 3:
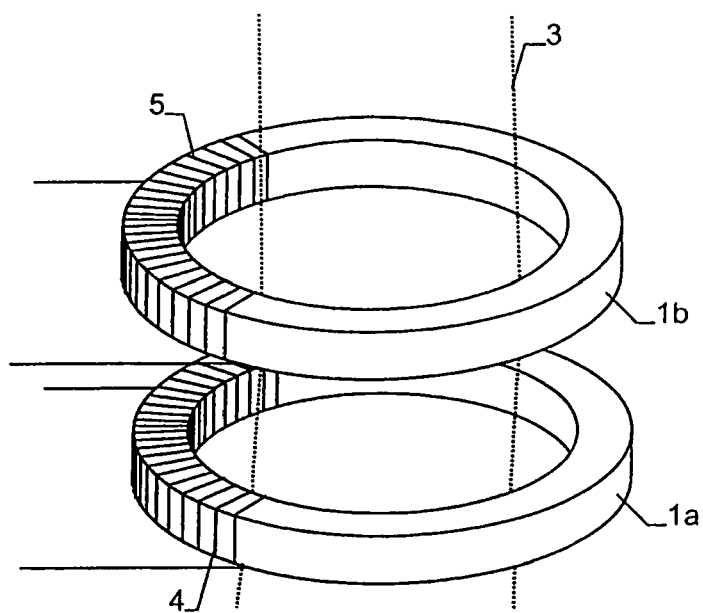
FIG. 3 shows another embodiment of the invention having two toroid coils.

FIG. 3 shows a further embodiment of the invention using two rings 1a, 1b having equal diameters and being arranged coaxially at a distance from each other. First coil 4 is arranged on ring 1a, second coil 5 is arranged on ring 1b. A housing or frame (not shown) is provided for holding the two rings at a predefined position in respect to each other.

The advantage of the embodiment of FIG. 3 lies in the fact that the coupling between the two coils occurs primarily via the electric field, which makes the voltage induced in second 6 coil more sensitive to changes of the dielectric properties of specimen 3.

Figure 4:
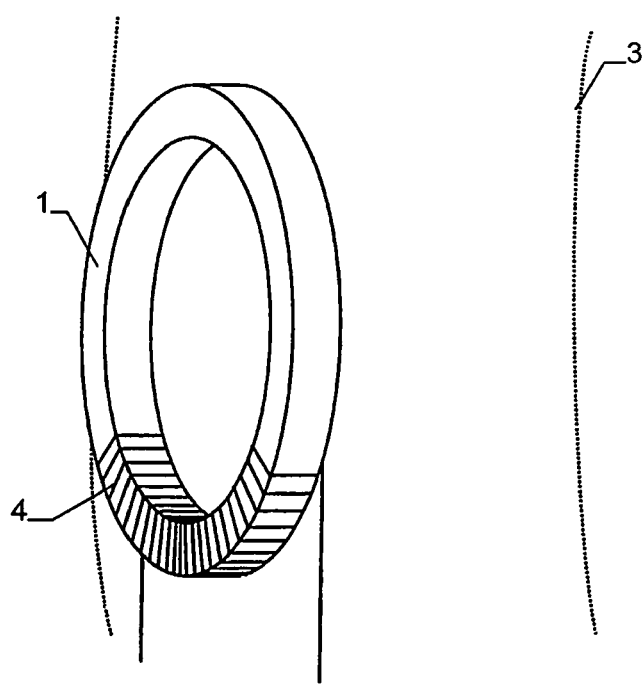
FIG. 4 shows a third embodiment of the invention in operation perpendicular the surface of a body part.

In the embodiments of FIGS. 1 and 3, specimen 3 extends through opening 2 of ring 1. However, it is also possible to make a measurement by placing ring 1 flat against a surface of specimen 3, such as shown in FIG. 4 for a single-coil ring. This arrangement, however, has the disadvantage that surface charges on specimen 3 play a more dominant role than in the arrangement of FIGS. 1 and 3.

In the embodiments shown so far, ring 1 forms a circle and has rectangular cross section. However, ring 1 may e.g. also have a shape different from a perfect circle and may can e.g. be ellipsoidal or polygonal. Similarly, its cross section may be of any other shape.

While there are shown and described presently preferred embodiments of the invention, it is to be distinctly understood that the invention is not limited thereto but may be otherwise variously embodied and practiced within the scope of the following claims.

The invention claimed is:

1. A device for the measurement of glucose levels characterized by
   at least one ring surrounding a central opening,
   a coil assembly comprising at least one coil wound around said ring, looped through said opening, having said ring as a core and generating a magnetic field extending along said ring,
   a current source generating an AC current in said coil and thereby generating said magnetic field and an alternating electric field,
   a detector for measuring a parameter depending on an inductance of said coil assembly and generating a measured signal, and
   a converter for converting the measured signal to a glucose level of a specimen located in said alternating electric field.

2. The device of claim 1 wherein said coil assembly comprises a first and a second coil wound around said ring and wherein said inductance is a mutual induction of said first and said second coil.

3. The device of claim 2 wherein said current source generates the AC current in the first coil and said detector measures a voltage or current induced in said second coil.

4. The device of claim 1 wherein said inductance is a self induction of said coil.

5. The device of claim 1 wherein said coil is a toroid coil.

6. The device of claim 1 wherein said ring has a magnetic permeability of at least 100.

7. The device of claim 1 wherein said ring has a magnetic permeability of at least 1000.

8. The device of claim 1 wherein said ring comprises a ferrite.

9. The device of claim 1 wherein said converter comprises a memory holding calibration data for converting the measured signal to the glucose level.

10. The device of claim 1, wherein the central opening is for receiving the specimen.

11. The device of claim 1 wherein said ring forms a circle.

12. The device of claim 1 wherein said ring comprises a first and a second part wherein said first and said second parts are at least at one point releasable connected to each other for opening said ring.

13. The device of claim 1 wherein said current source is designed for generating a substantially sinusoidal current.

14. The device of claim 1 comprising at least a first and a second ring, wherein the coil assembly comprises a first coil arranged on the first ring and a second coil arranged on the second ring.

15. The device of claim 14 wherein said rings are coaxial and located at a distance from each other.

16. A method for measuring a glucose level in a specimen comprising the steps of generating an AC current through a coil of a coil assembly, wherein said coil has a ring as a core, and thereby generating an AC magnetic and an alternating electric field, said ring surrounding a central opening and said coil being looped through said opening, placing a specimen in said electric field, measuring a parameter depending on an inductance of said coil assembly and generating a measured signal, and converting the measured signal to a glucose level of a specimen in said alternating electric field.

17. The method of claim 16 wherein said ring is laid around the specimen.

18. A method for measuring a glucose level in a specimen comprising the steps of providing an AC current through a coil wound about a ring so as to loop though a central opening of said ring for generating an AC magnetic field and an alternating electric field, placing a specimen in said alternating electric field, obtaining a measured signal depending on an inductance of said coil while said specimen is in said alternating electric field, and converting said measured signal to a glucose level of said specimen in said alternating electric field.

19. The method of claim 18, wherein obtaining said measured signal comprises measuring a parameter depending on said inductance of said coil and generating said measured signal therefrom.

* * * * *

UNITED STATES PATENT AND TRADEMARK OFFICE
CERTIFICATE OF CORRECTION

| | | |
|---|---|---|
| PATENT NO. | : 7,534,208 B2 | Page 1 of 1 |
| APPLICATION NO. | : 11/070859 | |
| DATED | : May 19, 2009 | |
| INVENTOR(S) | : Andreas Caduff et al. | |

It is certified that error appears in the above-identified patent and that said Letters Patent is hereby corrected as shown below:

Title page, (73), Assignee: "Max Link" should read --Solianis Holding AG--

Signed and Sealed this
Eighth Day of March, 2011

David J. Kappos
*Director of the United States Patent and Trademark Office*